US011130956B2

(12) United States Patent
Chen et al.

(10) Patent No.: US 11,130,956 B2
(45) Date of Patent: Sep. 28, 2021

(54) REDUCING THE TOXICITY OF AGROBACTERIUM ENDOTOXIN

(71) Applicant: ARIZONA BOARD OF REGENTS ON BEHALF OF ARIZONA STATE UNIVERSITY, Scottsdale, AZ (US)

(72) Inventors: Qiang Chen, Chandler, AZ (US); Ming Yang, Chandler, AZ (US); Huafang Lai, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/617,971

(22) PCT Filed: May 31, 2018

(86) PCT No.: PCT/US2018/035422
§ 371 (c)(1),
(2) Date: Nov. 27, 2019

(87) PCT Pub. No.: WO2018/226506
PCT Pub. Date: Dec. 13, 2018

(65) Prior Publication Data
US 2020/0190525 A1 Jun. 18, 2020

Related U.S. Application Data

(60) Provisional application No. 62/515,141, filed on Jun. 5, 2017.

(51) Int. Cl.
| | |
|---|---|
| C12N 15/74 | (2006.01) |
| A61K 39/39 | (2006.01) |
| C07K 14/195 | (2006.01) |
| C12N 9/10 | (2006.01) |
| C12P 19/12 | (2006.01) |
| A61K 39/00 | (2006.01) |

(52) U.S. Cl.
CPC ............ *C12N 15/743* (2013.01); *A61K 39/39* (2013.01); *C07K 14/195* (2013.01); *C12N 9/1029* (2013.01); *C12P 19/12* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 8,513,397 B2 | 8/2013 | Mason | |
| 8,663,950 B2 | 3/2014 | Chen | |
| 9,499,608 B2 | 11/2016 | Chen | |
| 9,506,079 B2 | 11/2016 | Mason | |
| 2005/0086714 A1* | 4/2005 | Yao | A01H 4/005 800/278 |
| 2017/0275639 A1 | 9/2017 | Chen | |
| 2018/0340181 A1 | 11/2018 | Chen | |

FOREIGN PATENT DOCUMENTS

| | | |
|---|---|---|
| WO | 2010025285 A1 | 3/2010 |
| WO | 2011085289 A1 | 7/2011 |
| WO | 2013006244 A1 | 1/2013 |
| WO | 2015113055 A2 | 7/2015 |
| WO | 2020247642 A1 | 12/2020 |

OTHER PUBLICATIONS

Sharypova et al. 2003 (Sinorhizobium meliloti acpXL Mutant Lacks the C28 hydroxylated Fatty Acid Moiety of Lipid A and Does Not Express a Slow Migrating Form of Lipopolysaccharide; Journal of Biological Chemistry; 278(15): 12946-12954) (Year: 2003).*
Wang et al. 2006 (Expression Cloning and Periplasmic Orientation of the Francisella novicida Lipid A 4'-Phosphatase LpxF; The Journal of Biological Chemistry vol. 281, No. 14, pp. 9321-9330). (Year: 2006).*
Klusener et al. 2010 (Proteomic and transcriptomic characterization of a virulence deficient phosphatidylcholine negative Agrobacterium tumefaciens mutant; Mol Genet Genomics 283: 575-589). (Year: 2010).*
Sharypova et al. 2003 (Sinorhizobium meliloti acpXL mutant lacks the C28 Hydroxylated Fatty Acid Moiety of Lipid A and Does Not Express a Show Migrating Form of Lipopolysaccharide; Jornal of Biological Chemistry; 278(15): 12946-54). (Year: 2003).*
Basu et al. 2002 (Expression Cloning and Characterization of the C28 Acyltransferase of Lipid A Biosynthesis in Rhizobium leguminosarum; J Biol Chem 277(32): 28959-28971) (Year: 2002).*
Silipo et al. 2004 (Full Structural characterization of the lipid A components from the Agrobacterium tumefaciens strain C58 lipopolysaccharide fraction; Glycobiology 14(9): 805-815) (Year: 2004).*
Haag et al. 2009 (The Sinorhizobium meliloti LpxXL and AcpXL Proteins Play Important Roles in Bacteroid Development within Alfalfa; Journal of Bacteriology 191 (14): 4681-4686). (Year: 2009).*
Aviezer, D., et al. "A plant-derived recombinant human glucocerebrosidase enzyme—a preclinical and phase I investigation." PLoS One 4.3 (2009): e4792.

(Continued)

*Primary Examiner* — Mary Maille Lyons
(74) *Attorney, Agent, or Firm* — Quarles & Brady LLP

(57) ABSTRACT

The present invention relates to the fields of genetically modified *Agrobacterium* strains, vaccine adjuvants, and generally molecular biology and immunology. Provided herein are modified *Agrobacterium* strains that produce lipopolysaccharide (LPS) having reduced toxicity or detoxified lipopolysaccharide, and methods of obtaining such strains for plant-based production of biologies. Also provided herein are uses of reduced or detoxified LPS as adjuvants suitable for clinical use.

12 Claims, 5 Drawing Sheets
Specification includes a Sequence Listing.

(56) References Cited

OTHER PUBLICATIONS

Chen, Q. et al. "The potential of plants as a system for the development and production of human biologics." F1000Research 5 (2016).
Chen, 2013, Virus-like Particle Vaccines for Norovirus Gastroenteritis. In M. Giese (Ed.), Molecular Vaccines (vol. 1, pp. 153-181). Vienna: Springer.
Chen, Q. et al. "Plant-derived virus-like particles as vaccines." Human vaccines & immunotherapeutics 9.1 (2013): 26-49.
Chen, Q. et a. "Agroinfiltration as an effective and scalable strategy of gene delivery for production of pharmaceutical proteins." Advanced techniques in biology & medicine 1.1 (2013).
Clarke, J. L., et al. "Lettuce-produced hepatitis C virus E1E2 heterodimer triggers immune responses in mice and antibody production after oral vaccination." Plant biotechnology journal 15.12 (2017): 1611-1621.
De Castro C., et al. "Lipopolysaccharide structures from Agrobacterium and Rhizobiaceae species." Carbohydrate Research 343.12 (2008): 1924-1933.
Dent, M., et al. "Plant-produced anti-dengue virus monoclonal antibodies exhibit reduced antibody-dependent enhancement of infection activity." The Journal of general virology 97.12 (2016): 3280.
Ferguson, G. P., et al. "Importance of unusually modified lipid A in Sinorhizobium stress resistance and legume symbiosis." Molecular microbiology 56.1 (2005): 68-80.
Giritch, A., et al. "Rapid high-yield expression of full-size IgG antibodies in plants coinfected with noncompeting viral vectors." Proceedings of the National Academy of Sciences 103.40 (2006): 14701-14706.
He, J., et al. "Generation and analysis of novel plant-derived antibody-based therapeutic molecules against West Nile virus." PLoS One 9.3 (2014): e93541.
Ingram, B. O., et al "*Escherichia coli* mutants that synthesize dephosphorylated lipid A molecules." Biochemistry 49.38 (2010): 8325-8337.
International Searching Authority. International Search Report and Written Opinion for application PCT/US2018/035422, dated Oct. 11, 2018.
Kersters, K., et al. "*Bordetella avium* sp. nov., isolated from the respiratory tracts of turkeys and other birds." International Journal of Systematic and Evolutionary Microbiology 34.1 (1984): 56-70.
Kong, Q., et al. "Palmitoylation state impacts induction of innate and acquired immunity by the *Salmonella enterica* serovar Typhimurium msbB mutant." Infection and immunity 79.12 (2011): 5027-5038.
Kong, Q., et al. "*Salmonella* synthesizing 1-monophosphorylated lipopolysaccharide exhibits low endotoxic activity while retaining its immunogenicity." The Journal of immunology 187.1 (2011): 412-423.
Kwon, K.-C., et al. "Low-cost oral delivery of protein drugs bioencapsulated in plant cells." Plant biotechnology journal 13.8 (2015): 1017.
Lai, H. et al. "Bioprocessing of plant-derived virus-like particles of Norwalk virus capsid protein under current Good Manufacture Practice regulations." Plant cell reports 31.3 (2012): 573-584.
Lai, H. et al. "Monoclonal antibody produced in plants efficiently treats West Nile virus infection in mice." Proceedings of the National Academy of Sciences 107.6 (2010): 2419-2424.
Lai, H. et al. "Robust production of virus-like particles and monoclonal antibodies with geminiviral replicon vectors in lettuce." Plant biotechnology journal 10.1 (2012): 95-104.
Leuzinger, K., et al. "Efficient agroinfiltration of plants for high-level transient expression of recombinant proteins." JoVE (Journal of Visualized Experiments) 77 (2013): e50521.
Phoolcharoen, W., et al. "A nonreplicating subunit vaccine protects mice against lethal Ebola virus challenge." Proceedings of the National Academy of Sciences 108.51 (2011): 20695-20700.
Phoolcharoen, W., et al. "Expression of an immunogenic Ebola immune complex in Nicotiana benthamiana." Plant biotechnology journal 9.7 (2011): 807-816.
Raetz, Crh, et al. "Lipopolysaccharide endotoxins." Annual review of biochemistry 71.1 (2002): 635-700.
Ramloch-Lorenz, K., et al. "Molecular characterization of the gene for carrot cell wall ß-fructosidase." The plant journal 4.3 (1993): 545-554.
Santi, L., et al. "An efficient plant viral expression system generating orally immunogenic Norwalk virus-like particles." Vaccine 26.15 (2008): 1846-1854.
Sawada, H., et al. "Proposal for rejection of Agrobacterium tumefaciens and revised descriptions for the genus *Agrobacterium* and for Agrobacterium radiobacter and Agrobacterium rhizogenes." International Journal of Systematic and Evolutionary Microbiology 43.4 (1993): 694-702.
Shaaltiel, Y., et al. "Plant-based oral delivery of ß-glucocerebrosidase as an enzyme replacement therapy for Gaucher's disease." Plant biotechnology journal 13.8 (2015): 1033-1040.
Silipo, A., et al. "Full structural characterization of the lipid A components from the *Agrobacterium tumefaciens* strain C58 lipopolysaccharide fraction." Glycobiology 14.9 (2004): 805-815.
Willems, A. et al. "Phylogenetic analysis of rhizobia and agrobacteria based on 16S rRNA gene sequences." International Journal of Systematic and Evolutionary Microbiology 43.2 (1993): 305-313.
Young, J. M., et al. "Classification and nomenclature of Agrobacterium and Rhizobium—a reply to Farrand et al. (2003)." Journal of Medical Microbiology 53.5 (2003): 1689-1695.
Zahringer et al., (1999) In D.C. Morrison, H. Brade, S. Opal, and S. Vogel (Eds.), Endotoxin in health and disease. Marcel Dekker, New York, pp. 93-114.
European Patent Office. Extended European Search Report for application 18812878.9, dated Feb. 12, 2021. 8 pages.
Bourassa, D.V. PhD Thesis: Rhizobium Lipid A Very Long Chain Fatty Acid Influence on Structure and Function. Nov. 13, 2013. Retrieved from the Internet: URL:https://getd.libs.uga.edu/pdfs/bourassa_dianna_v_201312_phd.pdf. p. 157-158.

\* cited by examiner acpXL/lpxF C58 acpXL C58

C58

MES buffer

SEQUENCE LISTING

```
<160> NUMBER OF SEQ ID NOS: 4

<210> SEQ ID NO 1
<211> LENGTH: 285
<212> TYPE: DNA
<213> ORGANISM: Agrobacterium tumefaciens

<400> SEQUENCE: 1
atgggcgtga cagctacatt cgacaaggtt gccgacatta tcgccgaaac cagcgaaatc      60
gaccgcgaaa ccattacgcc ggagagccac acgatcgacg atctgggcat cgacagcctc     120
gactttctcg atatcgtttt tgccatcgac aaggaattcg gcatcaagat tccgctcgag     180
cagtggacgc aggaagtcaa cgaaggcaag gtttccaccg aagaatactt cgtgctgaag     240
aacctctgcg ccaagatcga cgaattgcgc gccgccaagg gctga                     285

<210> SEQ ID NO 2
<211> LENGTH: 939
<212> TYPE: DNA
<213> ORGANISM: Agrobacterium tumefaciens

<400> SEQUENCE: 2
ttgaccacct tgaaattatt tctgacgcgg atcgtcctga aactggacca cttccggcag       60
tggctgatcg cgacattcgc ctttggcctt ctcaacctgc tgaagctttt tccggccgat     120
gcgggcattc gcgccacgga ccggctggcg cgcttgatag ggccgaaaac cggccgccac     180
aagctgatgc tctacaatct ggcgcgcgcc tttccggaaa aaaccgaaga ggagcggctg     240
gcgatcgcca tggacagctg ggccaatatg ggccggcttg cggcggaata tgtgtttctc     300
gaccggctgt tcgatttcga cccggaaaag aacgaacccg gccgcatcga agtcgagggt     360
acctcgacct ttctcgaatt gcgcgacaat ccgcggccct tcatcgtttt taccgcccat     420
agcggcaatt tcgaactgct gccggtagca ggctcggcct ttggtcttga tgtgacggtg     480
ctgttccggc cgccgaacaa tccctatgtg gccgacaagg tgttcaattt ccgcaaggaa     540
cgcatgggca atctcgtgcc gtcgcatgcc ggctcctcct tcgcgctggc gcggcaactg     600
gaaaagggcg gcggtgtggg tgtgcttgtc gaccagaagt tcggcaaggg gctgacgacg     660
```

| | |
|---|---|
| aagttcttcg ggcttgaggt tcgcaccaac ccgctgcttg ccaagctggt gcggcagttc | 720 |
| aattgcgatg tctatcccgc ccgctgcata cgccttccgg acaatcgcta caggctggaa | 780 |
| atagagccga aggttgaaat tccccgggat cagaagggca atgtcgatat tcaggcgacg | 840 |
| gcgcagcttc tgaacgacaa ggtggaaagc tgggtgcgag aatatcccgg ccaatggctt | 900 |
| tggtatcatg atcgctggga cgtgaagcac cagatttga | 939 |

<210> SEQ ID NO 3
<211> LENGTH: 666
<212> TYPE: DNA
<213> ORGANISM: Francisella tularensis

<400> SEQUENCE: 3

| | |
|---|---|
| gcaagatttc atatcatatt aggtttagtt gtttgttttt ttgcatggat attctttctt | 60 |
| atattcccga atttggatat acaattcgcg ggacattttt ataattcatc ggcacatcaa | 120 |
| tttattggtg ggtatgatgg ctttttagga ttttgcatt ggtttgctag attttttcca | 180 |
| atatttttt caataatagt gattttattt ctattaggat cgttattat cgataagttt | 240 |
| aagattaagt atagaaaagc tatattcttt attgcggtat gcttatggat aggtccaggt | 300 |
| ttggttgtta actatgtgtt taaagatcat tggggcgtc caagaccagt gatggtagag | 360 |
| caatttaatg gcgacaaaat ttttcaacca ccattcgtta tatcttcaca atgtgataaa | 420 |
| aactgctcct ttgtatgtgg tgatgcctca atgggatttt ggcttttgc atttatgcca | 480 |
| ttactagcta caagaaaaaa gaagcttgtt gcgtttatcg cagcagtagt tgctggtgga | 540 |
| ggtttgggat tgatgagaat gtcgcaagga gggcatttt ttagtgatgt tgttttctgt | 600 |
| ggcatatttg tgtatatctc aacctgggtg gtttatgcac taatgtatcg taaaaaagaa | 660 |
| tattga | 666 |

<210> SEQ ID NO 4
<211> LENGTH: 669
<212> TYPE: DNA
<213> ORGANISM: Francisella tularensis

<400> SEQUENCE: 4

| | |
|---|---|
| atggcaagat tcatatcat attaggttta gttgtttgtt ttttttgcatg gatattcttt | 60 |
| cttatattcc cgaatttgga tatacaattc gcgggacatt tttataattc atcggcacat | 120 |
| caatttattg gtgggtatga tggctttttta ggatttttgc attggtttgc tagattttt | 180 |
| ccaatatttt tttcaataat agtgatttta tttctattag gatcgttatt tatcgataag | 240 |
| tttaagatta agtatagaaa agctatattc tttattgcgg tatgcttatg gataggtcca | 300 |
| ggtttggttg ttaactatgt gtttaaagat cattggggc gtccaagacc agtgatggta | 360 |
| gagcaattta atggcgacaa aatttttcaa ccaccattcg ttatatcttc acaatgtgat | 420 |
| aaaaactgct cctttgtatg tggtgatgcc tcaatgggat tttggctttt tgcatttatg | 480 |
| ccattactag ctacaagaaa aaagaagctt gttgcgttta tcgcagcagt agttgctggt | 540 |
| ggaggtttgg gattgatgag aatgtcgcaa ggagggcatt ttttagtga tgttgttttc | 600 |
| tgtggcatat ttgtgtatat ctcaacctgg gtggtttatg cactaatgta tcgtaaaaaa | 660 |
| gaatattga | 669 |

REDUCING THE TOXICITY OF AGROBACTERIUM ENDOTOXIN

CROSS-REFERENCE TO RELATED APPLICATIONS

This application represents the national stage entry of PCT International Application No. PCT/US2018/035422, filed on May 31, 2018, and, claims priority to U.S. Provisional Application No. 62/515,141, filed Jun. 5, 2017, each of which is hereby incorporated by reference in its entirety for all purposes.

BACKGROUND

Lipopolysaccharide (LPS), also known as endotoxin, is produced by Gram-negative bacteria. It is a toxin and pyrogen that can trigger strong immune responses in the host, and contamination of biologics with LPS can lead to fever and uncontrolled production of pro-inflammatory cytokines in patients, often leading to septic shock. As a result, FDA and other regulatory agencies have stringent requirements for the elimination of the toxicity of LPS in biologics and other pharmaceutical products.

Agrobacterium-mediated genetic transformation is the most preferred method for genetic transformation in plants due to ease of implementation of method and cost effectiveness. For example, Agrobacterium strains are widely used to deliver target genes into plant cells for the production of biologics. As in other Gram-negative bacteria, lipopolysaccharide (LPS) is located on the outer membrane of an agrobacterium. LPS is not easily removed from certain plant-made biologics (PMBs). In particular, current methods of eliminating endotoxin from pharmaceutical manufacturing from plants involve expensive and labor-intensive purification processes, and these processes are inadequate for many target pharmaceuticals. As a result, there is a significant need for solutions to the problem of Agrobacteria-derived LPS contamination in PMBs.

BRIEF SUMMARY OF THE INVENTION

In the interest of providing a clear and concise summary, the following description references certain exemplary aspects and embodiments. Persons of ordinary skill in the art will, in view of the teachings in this application, readily recognize and appreciate that other aspects, embodiments, configurations, and variations of the technology disclosed herein are possible and that the exemplary aspects and embodiments described in this summary or elsewhere in this application are neither limiting nor exhaustive.

In a first aspect, provided herein is a genetically modified Agrobacterium bacterium, where the Agrobacterium bacterium comprises a functional deletion of one or more polypeptides required for synthesis of Very Long Chain Fatty Acid (VLCFA), and wherein the Agrobacterium bacterium is deficient in Lipopolysaccharide (LPS) toxicity relative to its parent strain. The functional deletion can be achieved by removal of at least a portion of the gene encoding AcpXL-dependent lipid A acyltransferase (lpxXL). The functional deletion can be achieved by removal of at least a portion of the gene encoding Acyl carrier protein (acpXL). The functional deletion can be achieved by removal of at least a portion of lpxXL and at least a portion of acpXL. In some cases, the genetically modified Agrobacterium comprises an exogenous nucleic acid encoding Lipid A 4'-phosphatase (LpxF). The exogenous nucleic acid encoding LpxF can be derived from Francisella tularensis, The Agrobacterium bacterium can be capable of or configured to infect plant cells, to mediate T-DNA transfer into plant cells, and to mediate T-DNA insertion into a plant cell genome. The Agrobacterium strain can be selected from the group consisting of Agrobacterium tumefaciens (A. tumefaciens) and Agrobacterium rhizogenes. The parent strain can be A. tumefaciens GV3101 or A. tumefaciens LBA4404, and the genetically modified bacterium retains the ability to mediate T-DNA transfer into plant cells, and to mediate T-DNA insertion into a plant cell genome. The parent strain can be A. tumefaciens (C58), and the genetically modified bacterium retains the ability to deliver tumor-inducing genes into plant cells.

In another aspect, provided herein is a method of reducing Lipopolysaccharide (LPS) toxicity in an Agrobacterium bacterium. The method can comprise or consist essentially of deleting or disrupting at least a portion of a gene encoding LpxXL or a gene encoding AcpXL in the bacterium, whereby a genetically modified Agrobacterium having reduced LPS toxicity relative to an Agrobacterium comprising said deleted or disrupted gene is obtained. In some cases, the method further comprises introducing an exogenous nucleic acid encoding Lipid A 4'-phosphatase (LpxF). The exogenous nucleic acid can be derived from Francisella tularensis. The Agrobacterium bacterium can be Agrobacterium tumefaciens strain GV3101 or LBA4404, wherein the genetically modified bacterium retains the ability to mediate T-DNA transfer into plant cells and to mediate T-DNA insertion into a plant cell genome. The Agrobacterium bacterium can be Agrobacterium tumefaciens strain C58, wherein the genetically modified bacterium retains the ability to deliver tumor-inducing genes into plant cells.

In a further aspect, provided herein is a method of reducing LPS toxicity in an Agrobacterium bacterium. The method can comprise or consist essentially of introducing into the bacterium an exogenous nucleic acid encoding LpxF, whereby a genetically modified Agrobacterium having reduced LPS toxicity relative to an Agrobacterium not comprising said exogenous nucleic acid is obtained. The exogenous nucleic acid encoding LpxF can be derived from Francisella tularensis. The Agrobacterium bacterium can be Agrobacterium tumefaciens strain GV3101 or LBA4404, wherein the genetically modified bacterium retains the ability to mediate T-DNA transfer into plant cells and to mediate T-DNA insertion into a plant cell genome. The Agrobacterium bacterium can be Agrobacterium tumefaciens strain C58, wherein the genetically modified bacterium retains the ability to deliver tumor-inducing genes into plant cells.

In another aspect, provided herein is a method for generating a LPS variant molecule having reduced endotoxicity and improved immunogenicity, the method comprising the steps of: (a) modifying an Agrobacterium strain according to a method described herein; and (b) allowing the modified Agrobacterium strain to grow under conditions to produce a LPS variant molecule having reduced endotoxicity and improved immunogenicity compared to an LPS molecule from an Agrobacterium strain not modified according to step (a). In some cases, the method further comprises isolating the LPS variant molecule.

In a further aspect, provided herein is a lipopolysaccharide (LPS) isolated from a genetically modified Agrobacterium obtained according to a method described herein, wherein the LPS exhibits reduced toxicity relative to LPS produced by a wild-type Agrobacterium or an Agrobacterium that is not so genetically modified.

Also provided herein is an adjuvant comprising an immunostimulatory quantity of a reduced toxicity LPS as provided herein and a pharmaceutically acceptable carrier.

Also provided herein is an immunogenic composition comprising a polynucleotide encoding an antigen capable of eliciting an immune response and the adjuvant comprising an immunostimulatory quantity of a reduced toxicity LPS.

DETAILED DESCRIPTION

Figure 1A:
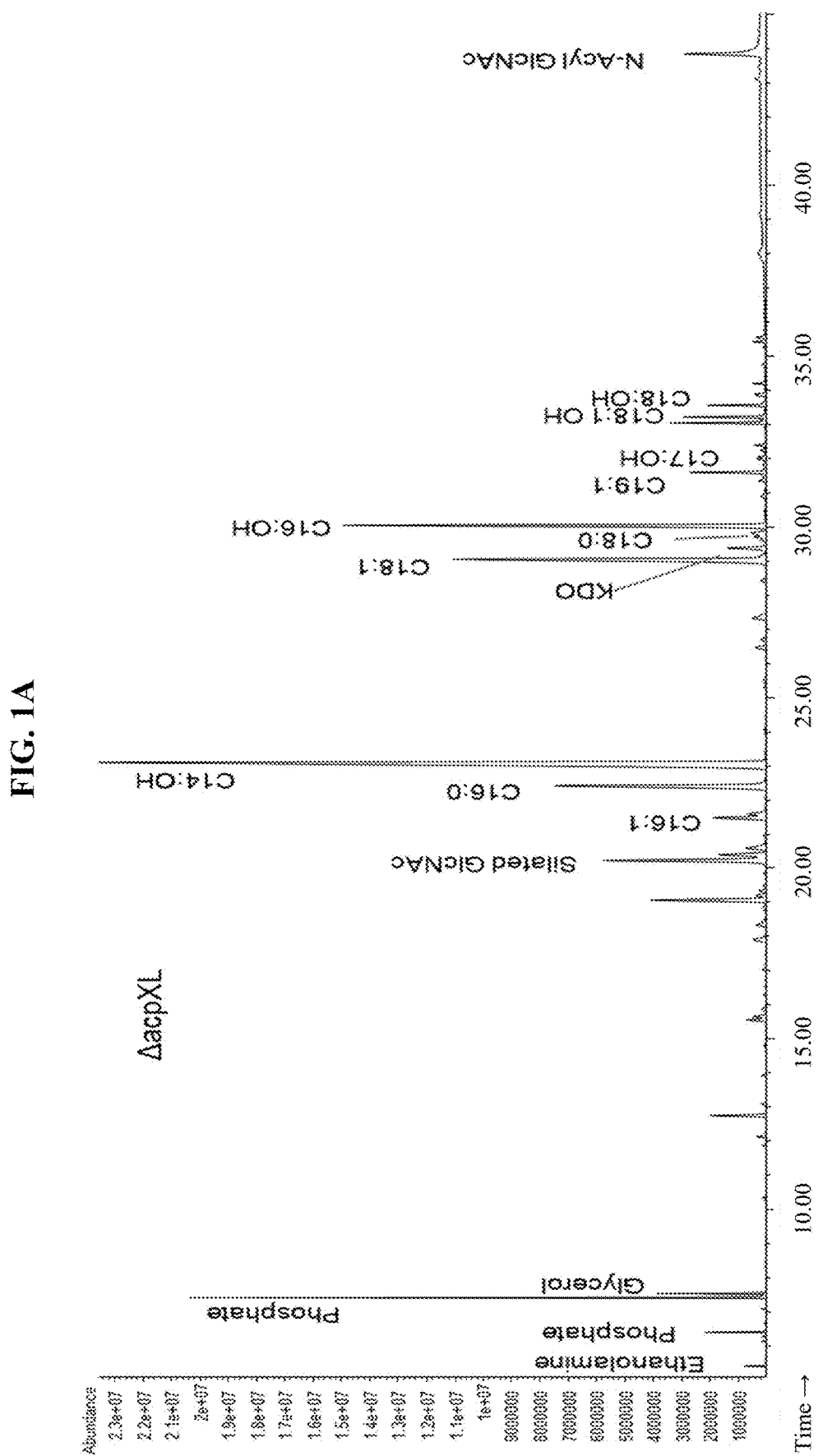
FIG. 1A presents fatty acid composition analysis of Lipid A released from acpXL mutants. The gas chromatography/mass spectrometry (GCMS) chromatogram of Lipid A is shown. Notice the lack of the VLCFA in the results.
Figure 1B:
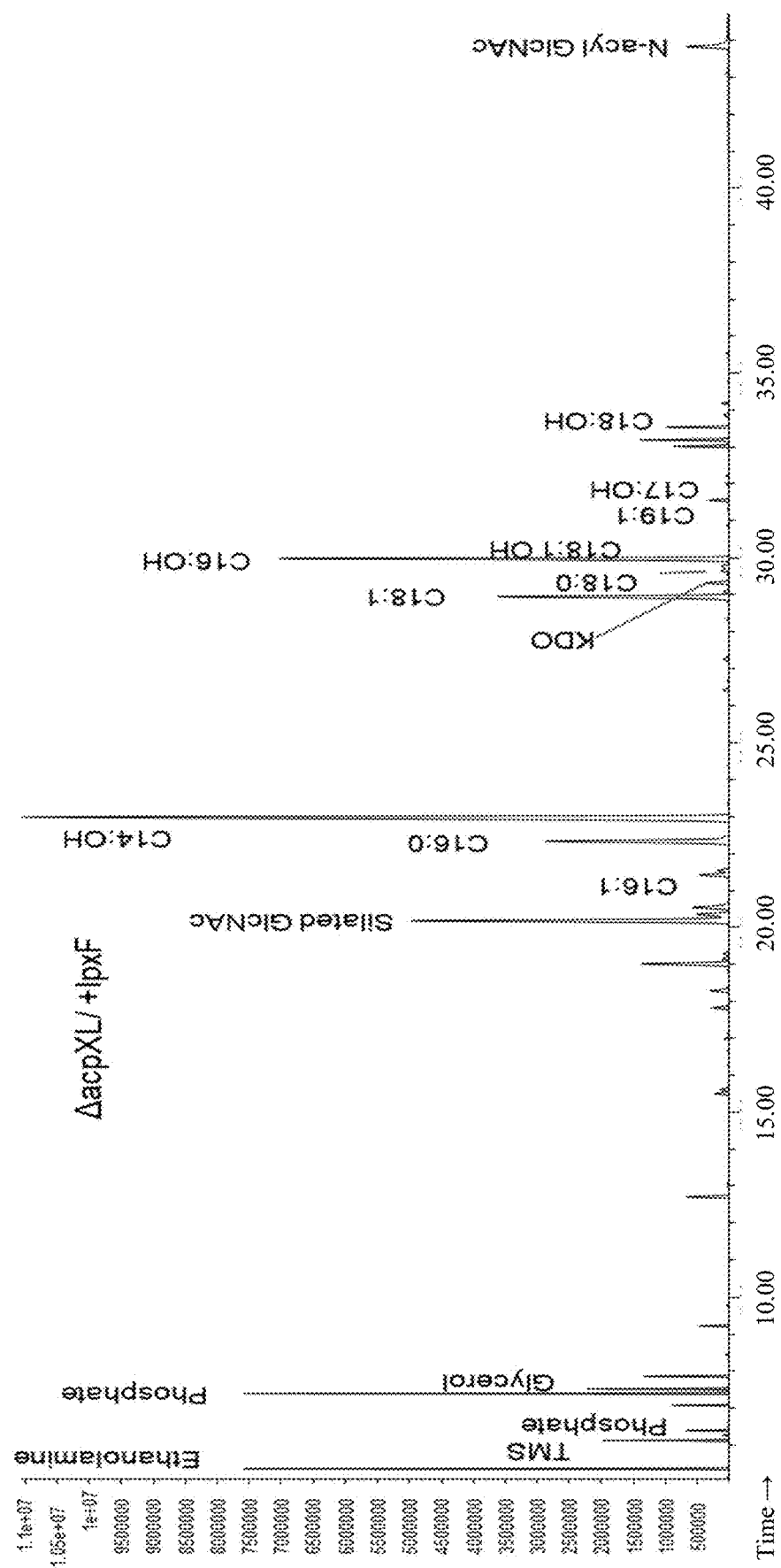
FIG. 1B presents fatty acid composition analysis of Lipid A released from acpXL/lpxF mutants. The gas chromatography/mass spectrometry (GCMS) chromatogram of Lipid A is shown. Notice the lack of the VLCFA in the results.
Figure 2:
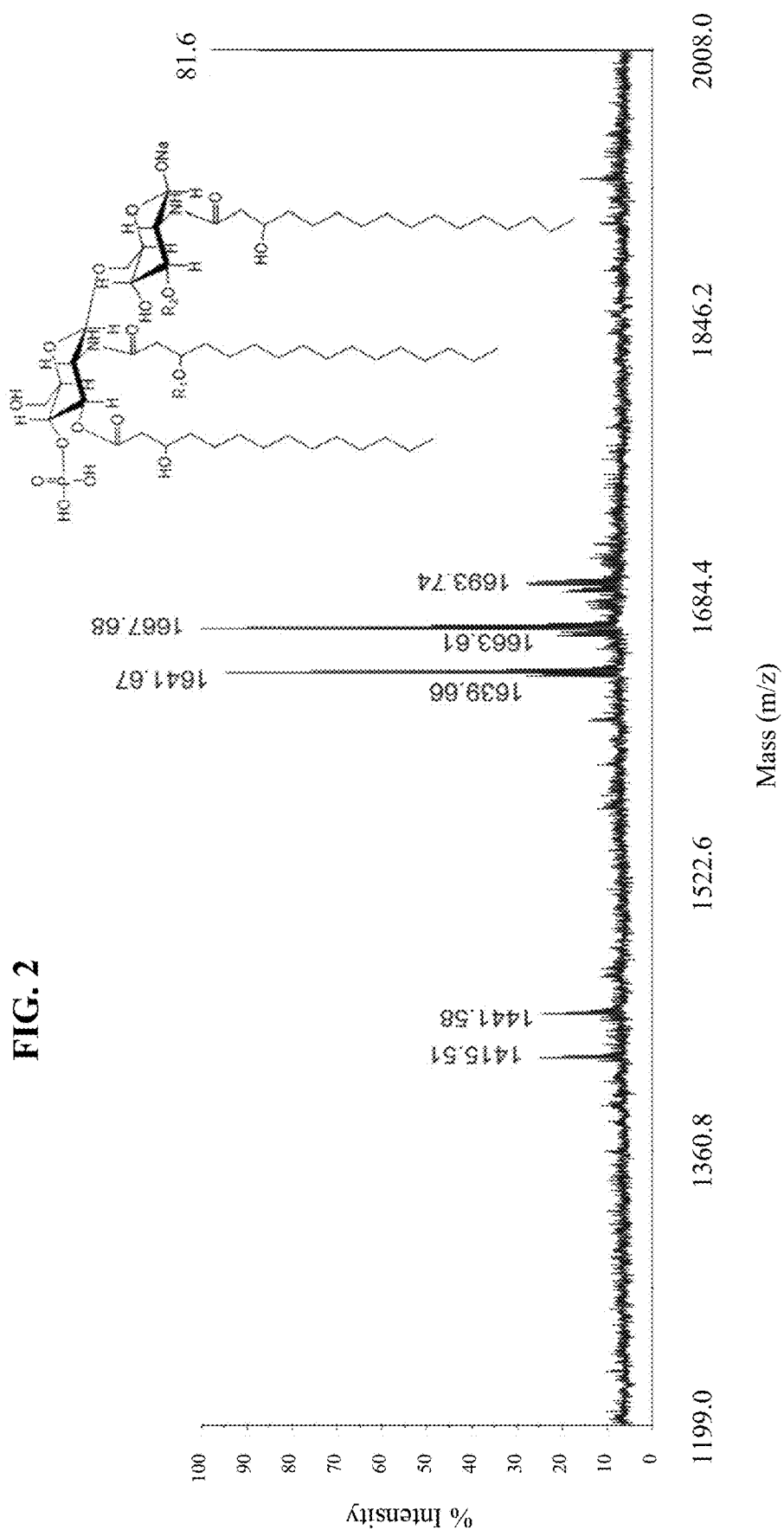
FIG. 2 presents MALDI-TOF spectra of the acpXL mutant. Inset: image of the major Lipid A species for the mutant is shown. R1 can be $H^+$ in the tetra-acylated cluster or either 16:0, 18:1 in the penta-acylated cluster. R2 can be $H^+$ in the tetra-acylated cluster and b-OHC14:0 in the penta-acylated cluster.
Figure 3:
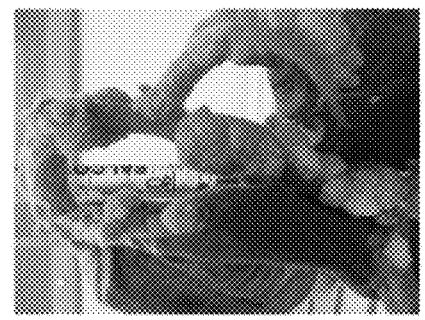
FIG. 3 demonstrates crown gall-like tumor formation by C58 variants on *Nicotiana benthamiana* plants. The parent C58 or acpXL, acpXL/lpxF *A. tumefaciens* variants was injected into the stem of *N. benthamiana* plants along with a IVIES buffer negative control. Tumor formation was monitored and photographed 30 days after *Agrobacterium* injection.
Figure 3:
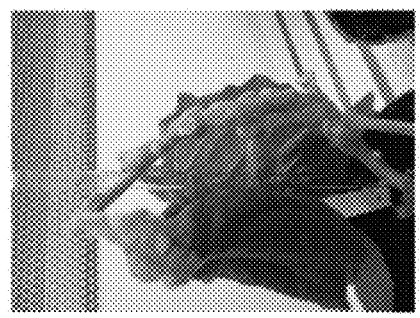
Figure 3:
Figure 3:
Figure 4:
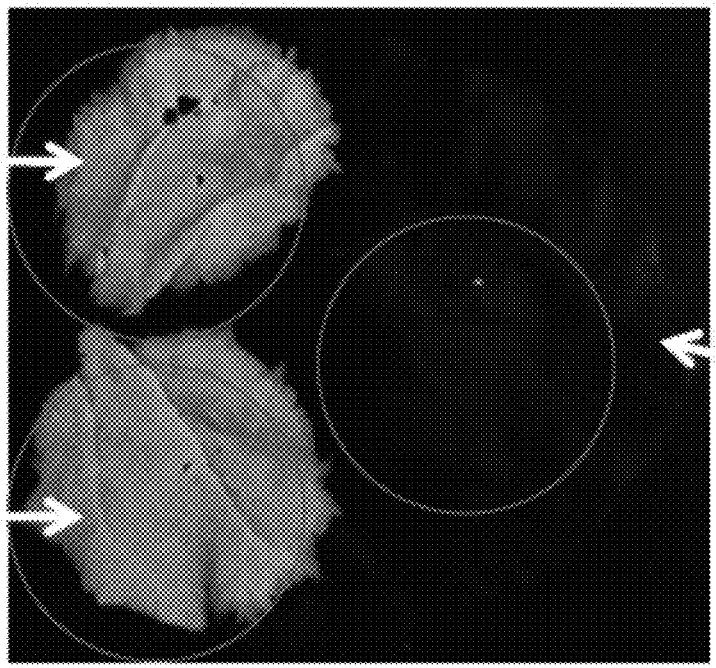
FIG. 4 demonstrates expression of green fluorescent protein (GFP) in *Nicotiana benthamiana* plant leaves. GFP gene was transformed into the parent GV3101, acpXL, and acpXL/lpxF *A. tumefaciens* strains. *A. tumefaciens* or IVIES buffer alone (negative control) was then infiltrated into different areas of a *N. benthamiana* leaf. GFP expression was detected 4 days after agroinfiltration.
Figure 4:
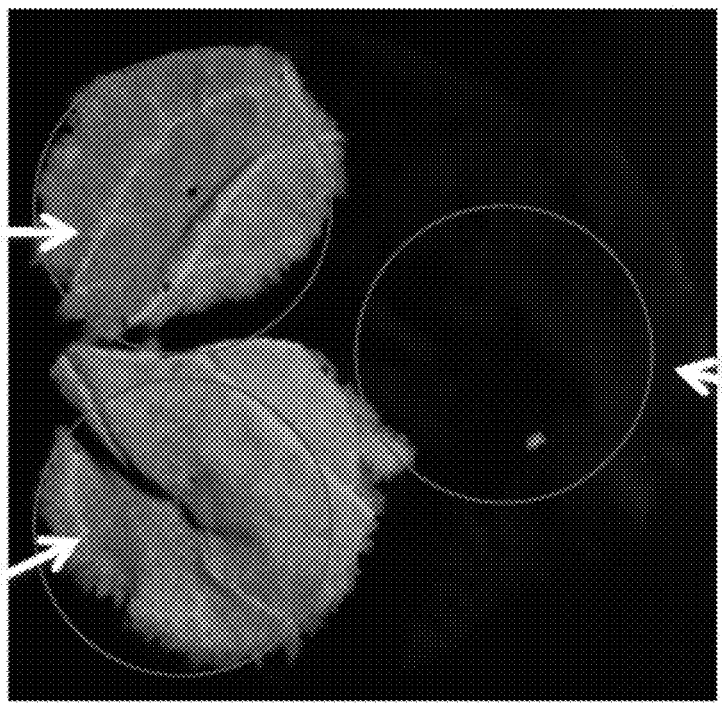

The compositions and methods provided herein are based at least in part on the inventors' development of modifications to genes encoding polypeptides involved in lipid A synthesis; the developed modifications alter the toxicity of Lipopolysaccharide (LPS). LPS is a potent activator of immune responses via distinct stimulatory mechanisms. However, LPS is inherently toxic to humans and animals due to hyper-activation of inflammatory immune responses. LPS generally has three domains: lipid A, core oligosaccharide, and O-antigen. The lipid A component is the effective toxic part of LPSs and is responsible for LPS's immunostimulatory activity of Gram-negative bacteria. Without being bound to any particular theory or mode of action, it is expected that *Agrobacterium* LPS comprising tetra- or pentaacylated or monophosphorylated lipid A species will exhibit significantly reduced toxicity and reduced, comparable, or improved immunogenicity. Since the LPS comprising tetra- or pentaacylated or monophosphorylated lipid A species is produced in *Agrobacterium*, which are plant-pathogenic bacteria and not pathogens of human or animal cells, LPS having reduced toxicity is suitable for use as an adjuvant with reduced or eliminated risk of endotoxicity and free of (or substantially free of) contamination by bacterial components or by-products of human pathogenic bacteria.

Advantages of the genetically modified Agrobacteria provided herein are multifold. For example, *Agrobacterium* variants having reduced LPS toxicity or expressing a detoxified LPS are advantageous for the production of safer plant-based biologics for use in humans and non-human animals. By reducing or eliminating the endotoxicity of LPS toxin before it is produced in the bacterial cell and, thus, reducing or eliminating the need for expensive and labor-intensive purification processes of biomolecules made using cell comprising the variant Agrobacteria, the variants expedite drug approval, enhance drug safety, and reduce biologic production costs. For adjuvant production, *Agrobacterium* is a plant-specific pathogen, so producing an adjuvant using agrobacteria is safer than production using human pathogenic bacteria. Therefore, genetically modified Agrobacteria provided herein are advantageous for the production of low-toxicity or detoxified LPS that is a safe and effective adjuvant suitable for approval by the Food and Drug Administration (FDA) for clinical applications.

Definitions

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application are specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the terms "polynucleotide," "nucleic acid," and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product. As used herein, the term "coding sequence" refers to a nucleic acid sequence that encodes a specific amino acid sequence.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

As used herein, the term "modification" can refer to a change (e.g., disruption) in a polynucleotide disclosed herein that results in reduced, substantially eliminated or eliminated activity of a polypeptide encoded by the polynucleotide, as well as a change in a polypeptide disclosed herein that results in reduced, substantially eliminated, or eliminated activity of the polypeptide. Alternatively, the term "modification" can refer to a change in a polynucleotide disclosed herein that results in increased or enhanced activity of a polypeptide encoded by the polynucleotide, as well as a change in a polypeptide disclosed herein that results in increased or enhanced activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof.

As used herein, the terms "genetically modified" and "genetically engineered" are used interchangeably and refer to a prokaryotic or eukaryotic cell that has been modified to comprise a non-naturally occurring nucleic acid molecule that has been created or modified by the hand of man (e.g., using recombinant DNA technology) or is derived from such a molecule (e.g., by transcription, translation, etc.). An *Agrobacterium* bacterium that contains an exogenous, recombinant, synthetic, and/or otherwise modified polynucleotide is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart). Procedures for producing genetically engineered cells are generally known in the art, and are described in Sambrook et al, *Molecular Cloning, A Laboratory Manual*, Cold Spring Harbor Press, Cold Spring Harbor, N.Y. (1989), incorporated herein by reference.

The term "expression," as used herein refers to the biosynthesis of a gene product. For example, in the case of a structural gene, expression involves transcription of the structural gene into mRNA and—optionally—the subsequent translation of mRNA into one or more polypeptides. The term "expression" also refers to the transcription and stable accumulation of sense (mRNA) or antisense RNA derived from a DNA. As used herein, the term "overexpression" refers to expression that is higher than endogenous expression of the same gene or a related gene. Thus, a heterologous gene is "overexpressed" if its expression is higher than that of a comparable endogenous gene.

The term "*Agrobacterium*" as used herein refers to a soil-borne, Gram-negative, rod-shaped phyto-pathogenic bacterium. *Agrobacterium* together with *Rhizobium, Sinorhizobium*, and *Allorhizobium* are genera within the bacterial family Rhizobiaceae (Kersters and De Ley. 1984), which has been included in the alpha-2 subclass of Proteobacteria on the basis of ribosomal characteristics (Willems and Collins. 1993). The species of *Agrobacterium, Agrobacterium tumefaciens* (syn. *Agrobacterium radiobacter*), *Agrobacterium rhizogenes, Agrobacterium rubi*, and *Agrobacterium vitis*, together with *Allorhizobium undicola*, form a monophyletic group with all *Rhizobium* species, based on comparative 16S rDNA analyses (Sawada 1993, Young 2003).

Compositions

In a first aspect, provided herein is a genetically modified *Agrobacterium* bacterium exhibiting reduced LPS toxicity or having a detoxified LPS. In certain embodiments, an *Agrobacterium* bacterium is genetically modified to produce LPS comprising tetra-acylated lipid A or penta-acylated lipid A with one of the acyl chains being shorter than acyl chains of an unmodified *Agrobacterium* strain. In such cases, an *Agrobacterium* bacterium is genetically modified to comprise a functional deletion of a polypeptide involved in lipid A synthesis. Structures of the main Lipid A components in *Agrobacterium tumefaciens* strain C58 and other Rhizobiaceae species are known in the art (Silipo et al., *Glycobiology* (2004) 14(9):805-815; Castro et al., Carbohydrate Res. (2008) 343:1924-1933). Lipid A is a glycolipid with a highly heterogeneous but rather conservative structure, typically composed of a 2-deoxy-2-amino-glucose (glucosamine, GlcN) disaccharide backbone, phosphorylated at positions 1 and 4' (Raetz et al., *Annu. Rev. Biochem.* 71:635-700 (2002); Zahringer et al., (1999) In D. C. Morrison, H. Brade, S. Opal, and S. Vogel (Eds.), Endotoxin in health and disease. Marcel Dekker, New York, pp. 93-114). The bis-phosphorylated glucosamine disaccharide backbone is modified with 5 acyl chains (penta-acylated): two unsubstituted 14:0 (3-OH) fatty acids in ester, two 16:0 (3-OH) in amide linkage, and the one on GlcN II was O-acylated by a long chain fatty acid, 28:0 (27-OH) (called a Very Long Chain Fatty Acid (VLCFA)). VLCFAs, which are fatty acids having carbon (C) chain lengths of greater than 20, are in turn esterified by a 3-hydroxy-butyroyl residue at its hydroxyl group.

In some cases, a functional deletion is achieved by deleting or disrupting (e.g., by mutation of a coding sequence) at least a portion of the acpXL gene, whereby the genetically modified bacterium does not express a functional AcpXL polypeptide. The acpXL gene (SEQ ID NO:1) encodes the C28-acyl carrier protein AcpXL. This polypeptide is required for synthesis of VLCFAs in Agrobacteria. Modified *Agrobacterium* comprising an acpXL deletion may produce tetra-acylated lipid A lacking VLCFA. In some cases, modified *Agrobacterium* comprising acpXL deletion may produce new variants of penta-acylated lipid A with VLCFA replaced by a shorter acyl chain (16:0 or 18:1), or a mixture of tetra- and penta-acylated lipid A (FIG. 1 and FIG. 2).

In some cases, a functional deletion is achieved by deleting or disrupting (e.g., by mutation of a coding sequence) at least a portion of the lpxXL gene, or at least a portion of both lpxXL and acpXL genes (i.e., to obtain a double mutant), whereby the genetically modified bacterium does not express a functional LpxXL and/or AcpXL polypeptide. The lpxxl gene encodes the C28-acyl transferase (SEQ ID NO:2). These polypeptides are required for synthesis and transfer of VLCFAs in Agrobacteria.

In some cases, genetic modifications are made in the wild-type (WT) *Agrobacterium tumefaciens* C58 strain. In other cases, genetic modifications are made in *Agrobacterium tumefaciens* strains GV3101 or LBA4404, which are engineered strains for delivery of transgenes into plant cells for biotechnology applications. The toxicity of LPS in both the WT and engineered strain having deletions or disruptions in one or both of genes lpxXL and acpXL is significantly reduced as determined in cell-based assays. In addition, acpXL variants in the *Agrobacterium tumefaciens* C58 strain retain the ability to deliver tumor-inducing genes into plants as evidenced by the retained capacity to produce crown gall-like structures on tobacco leaves (FIG. 3). AcpXL variants in the *Agrobacterium tumefaciens* GV3101 strain retain the ability to deliver transgenes into plants (e.g., the ability to mediate T-DNA transfer into plant cells and T-DNA insertion into a plant cell genome). For example, polypeptides and other biological molecules such as monoclonal antibodies, virus-like particle vaccines, and detectable reporter proteins (e.g., green fluorescent protein and variants thereof) can be produced robustly when transgenes encoding such biological molecules are delivered by the genetically modified Agrobacteria (FIG. 4).

In some cases, an *Agrobacterium* bacterium is genetically modified to produce LPS containing monophosphorylated lipid A. In such cases, an *Agrobacterium* bacterium is genetically modified to introduce an exogenous lpxF gene which encodes Lipid A 4'-phosphatase (LpxF), a 4'-phosphatase that dephosphorylates the phosphate group on the 4' carbon (i.e., the 4'-phosphate moiety) from lipid IV(A) (a tetra-acylated precursor of lipid A) and from penta-acylated lipid A, but not from hexa-acylated lipid A (as is found in *E. coli*). LpxF does not dephosphorylate phosphatidic acid, phosphatidylglycerophosphate, or the 1'-phosphate group of lipid A and lipid A precursors. In some cases, the exogenous lpxF gene is derived from the gene encoding LpxF in the bacterium *Francisella tularensis* (SEQ ID NO:3; see also SEQ ID NO:4 (comprising ATG for expression in *Agrobacterium*)). The toxicity of LPS in both the WT and engineered strain genetically modified to express LpxF is significantly reduced.

In some cases, genetic modifications to introduce expression of LpxF are made in the wild-type (WT) *Agrobacterium tumefaciens* C58 strain. In other cases, such genetic modifications are made in *Agrobacterium tumefaciens* strains GV3101 or LBA4404. In addition, lpxF variants in the *Agrobacterium tumefaciens* C58 strain retain the ability to deliver tumor-inducing genes into plants as evidenced by the retained capacity to produce crown gall-like structures on tobacco leaves, and lpxF variants in the *Agrobacterium tumefaciens* GV3101 strain retain the ability to deliver transgenes into plants e.g., for biotechnology purposes.

In some cases, *Agrobacterium* double mutants comprising deletions or disruptions to at least a portion of genes acpXL and lpxF are produced by inserting an exogenous nucleic acid encoding LpxF (e.g., the lpxF gene derived from *Francisella tularensis*) into the region of the genome comprising the coding sequence for AcpXL. In this manner, the gene encoding acpXL is disrupted and the genetically modified variant does not express a functional AcpXL polypeptide, which is required for VLCVA synthesis, but does express LpxF.

In some cases, genetic modifications producing acpXL/lpxF double mutants are made in the wild-type (WT) *Agrobacterium tumefaciens* C58 strain. In other cases, genetic modifications producing acpXL/LpxF double mutants are made in the engineered strains *Agrobacterium tumefaciens* GV3101 or LBA4404. The toxicity of LPS in the WT strain and the engineered strains comprising the acpXL/lpxF double mutations was significantly reduced as evidenced by in cell-based assays. In addition, acpXL/lpxF double mutants in the *Agrobacterium tumefaciens* C58 strain retain the ability to deliver tumor-inducing genes into plants as evidenced by the retained capacity to produce crown gall-like structures on tobacco leaves (FIG. 3), and acpXL/lpxF double mutants in the *Agrobacterium tumefaciens* GV3101 strain retain the ability to deliver transgenes into plants (FIG. 4) (e.g., the ability to mediate T-DNA transfer into plant cells and T-DNA insertion into a plant cell genome).

While certain example *Agrobacterium* strains are described herein, the functionality discussed could be moved to other *Agrobacterium* strains with the same criteria, e.g., other strains which are deficient in LPS toxicity, expressing a detoxified LPS, or could be made deficient in LPS toxicity. For example, modified Agrobacteria can be produced using *Agrobacterium tumefaciens* (syn. *Agrobacterium radiobacter*), *Agrobacterium rhizogenes, Agrobacterium rubi*, and *Agrobacterium vitis*. Examples of other strains that could be used with the strains and methods described herein include, but are not limited to, *Agrobacterium tumefaciens* strain C58, *Agrobacterium tumefaciens* strain GV3101, *Agrobacterium tumefaciens* strain GV3100, *Agrobacterium tumefaciens* strain GV3850, *Agrobacterium tumefaciens* strain GV2260, *Agrobacterium tumefaciens* strain A136, *Agrobacterium tumefaciens* strain A136, *Agrobacterium tumefaciens* strain Chry5, *Agrobacterium rhizogenes* strains, *Agrobacterium tumefaciens* strain EHA101, *Agrobacterium tumefaciens* strain EHA105, *Agrobacterium tumefaciens* strain MOG101, *Agrobacterium tumefaciens* strain 649, and *Agrobacterium tumefaciens* strain T37.

Any appropriate method of genetically modifying genes in an *agrobacterium* can be used to produce the variants described herein. For example, disruption of the target gene(s) can be achieved by homologous recombination. As used herein, the term "recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule. As used herein, the term "homologous recombination" refers to recombination occurring between two DNA base sequences in a region where they have similar sequences or homologous sequences. As is well known to those skilled in the field of molecular biology, large repeated sequences such as these are preferred targets for intramolecular recombination that leads eventually to DNA deletions and other rearrangements.

In another aspect, provided herein is lipopolysaccharide (LPS) isolated from a *Agrobacterium* strain modified as described herein, where isolated LPS exhibits reduced toxicity relative to LPS produced by a wild-type *Agrobacterium* strain or an *Agrobacterium* strain that is not so genetically modified. Such reduced toxicity LPS is well-suited for use in an adjuvant. For example, reduced toxicity LPS produced by a modified *Agrobacterium* strain can be provided as with a pharmaceutically acceptable carrier as a pharmaceutical composition.

In some cases, the adjuvant comprises an immunostimulatory quantity of reduced toxicity LPS and a pharmaceutically acceptable carrier. As used herein, the term "immunostimulatory" refers to the capacity of an agent (e.g., reduced toxicity LPS produced by an *Agrobacterium* strain modified as described herein) to elicit or induce an immunogenic response in an animal. The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N. J. current edition).

In some cases, a reduced LPS-containing adjuvant is provided with an antigen or a polynucleotide encoding an antigen capable of eliciting an immune response. Antigens useful for the compositions described herein can be derived from a cell, bacteria, or virus particle, or portion thereof. As used herein, "antigen" refers to a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell mediated. In the event the material to which the immunogenic response is to be directed is poorly antigenic, it may be conjugated to a carrier such as albumin or to a hapten, using standard covalent binding techniques, for example, with one of the several commercially available reagent kits. Examples of antigens include viral proteins such as influenza proteins and hepatitis B proteins; and bacterial proteins and lipopolysaccharides such as gram-negative bacterial cell wall and surface proteins.

The adjuvant can also be covalently conjugated with the antigen in accordance with methods well-known to those skilled in the art, usually by covalent linkage between an amino or carboxyl group on the antigen and one or more side groups on the adjuvant. Although in the preferred embodiment the adjuvant and antigen of the vaccine composition are administered simultaneously, in an alternative embodiment, the adjuvant and antigen are administered separately to the same site or to nearby sites. The adjuvant serves to attract cells of the immune system to the site where they then act upon the antigen.

The immunogenic composition can be administered as a vaccine by any method known to those skilled in the art that elicits an immune response, including parenterally, orally, or by transmembrane or transmucosal administration.

Methods

In another aspect, provided herein are methods for reducing lipopolysaccharide (LPS) toxicity in an *Agrobacterium* bacterium. Generally, the methods comprise deleting or disrupting genes that encode proteins that perform certain functions in the LPS synthetic pathway (which encompasses synthesis of all three LPS domains: lipid A, core oligosaccharide, and O-antigen), or introducing genes from other bacteria that have functions in the LPS synthetic pathway, or a combination of both deleting genes and introducing new genes in the LPS synthetic pathway.

In certain embodiments, the method comprises deleting or disrupting at least a portion of a gene encoding LpxxL or a gene encoding AcpXL in the bacterium, whereby a genetically modified *Agrobacterium* having reduced LPS toxicity relative to an *Agrobacterium* comprising said deleted or disrupted gene is obtained. In some cases, the method further comprises introducing an exogenous nucleic acid encoding Lipid A 4'-phosphatase (LpxF) into the *Agrobacterium*. Preferably, the exogenous nucleic acid encoding LpxF is derived from *Francisella tularensis*. The genetic modifications can be made in *Agrobacterium tumefaciens* strain GV3101 or LBA4404, where the genetically modified bacterium retains the ability to mediate T-DNA transfer into plant cells and to mediate T-DNA insertion into a plant cell genome. In other cases, the genetic modifications are made in *Agrobacterium tumefaciens* strain C58, where the genetically modified bacterium retains the ability to deliver tumor-inducing genes into plant cells.

In another aspect, provided herein is a method of reducing LPS toxicity in an *Agrobacterium* bacterium. In certain embodiments, the method comprises introducing into the bacterium an exogenous nucleic acid encoding LpxF, whereby a genetically modified *Agrobacterium* having reduced LPS toxicity relative to an *Agrobacterium* not comprising said exogenous nucleic acid is obtained. The exogenous nucleic acid encoding LpxF can be derived from *Francisella tularensis*. The genetic modifications can be made in *Agrobacterium tumefaciens* strains GV3101 or LBA4404, where the genetically modified bacterium retains the ability to mediate T-DNA transfer into plant cells and to mediate T-DNA insertion into a plant cell genome. In other cases, the genetic modifications are made in *Agrobacterium tumefaciens* strain C58, where the genetically modified bacterium retains the ability to deliver tumor-inducing genes into plant cells.

In a further aspect, provided herein is a method for generating a LPS variant molecule having reduced endotoxicity and improved immunogenicity, the method comprising the steps of: (a) modifying an *Agrobacterium* strain according to the methods provided herein; and (b) allowing the modified *Agrobacterium* strain to grow under conditions to produce a LPS variant molecule having reduced endotoxicity and improved immunogenicity compared to an LPS molecule from an *Agrobacterium* strain not modified according to step (a). Preferably, the method also comprises isolating the variant LPS from the genetically modified *Agrobacterium* strain. LPS molecules can be isolated by conventional means. In some cases, LPS is extracted from an exponential phase culture of the genetically modified *Agrobacterium*. The extracted LPS can be purified and quantified according to well-known procedures. As described herein, LPS isolated from a genetically modified *Agrobacterium* will exhibit reduced toxicity and improved immunogenicity relative to LPS produced by a wild-type *Agrobacterium* or an *Agrobacterium* that is not so genetically modified.

In some cases, the adjuvant comprises an immunostimulatory quantity of reduced toxicity LPS obtained according to the methods provided herein and a pharmaceutically acceptable carrier, excipient, or vehicles to provide a liquid preparation. Auxiliary substances, such as wetting or emulsifying agents, pH buffering substances and the like, may be present in the excipient or vehicle. These carriers, excipients, vehicles and auxiliary substances are generally pharmaceutical agents that do not induce an immune response in the individual receiving the composition, and which may be administered without undue toxicity. Pharmaceutically acceptable carriers and excipients include, but are not limited to, liquids such as water, saline, polyethyleneglycol, hyaluronic acid, glycerol and ethanol.

In some cases, the adjuvant is used to prepare an immunogenic composition for vaccine delivery. The immunogenic composition can comprise an antigen (e.g., a polypeptide, a polynucleotide encoding an antigen, or a combination of both) capable of eliciting an immune response and, as an adjuvant, an immunostimulatory quantity of reduced toxicity LPS.

In another aspect, provided herein are methods of producing plant-based biologics using reduced endotoxicity *Agrobacterium* as described herein. In some cases, the methods employ "agroinfiltration," which is the delivery of exogenous DNA-carrying Agrobacteria into the intracellular space of a plant tissue (e.g., plant leaf), thus allowing delivery of exogenous nucleic acids into plant cell genomes.

Producing Virus-Like Particle Based Vaccines:

VLPs resemble viruses, but are non-infectious because they contain no viral genetic material. The expression of viral structural proteins, such as Envelope or Capsid, can result in the self-assembly of virus like particles (VLPs). VLPs are useful as vaccines because they contain repetitive, high density displays of viral surface proteins that present conformational viral epitopes that can elicit strong T cell and B cell immune responses. Since VLPs cannot replicate, they provide a safer alternative to attenuated viruses. VLPs of different viral origin have been successfully produced in plants. However, since VLPs have a dynamic structure (can breathe with its pores) LPS can be trapped inside the VLPs and difficult to remove. In such instance, the gene of capsid or envelope protein that can form VLPs (for example Hepatitis B core antigen—HBcAg or norovirus capsid protein NVCP) can be cloned into plant expression vectors, and then transformed into the mutant *A. tumefaciens* GV3101 or LBA4404 strain by electroporation as previously described (Santi et al., *Vaccine*, 26(15), 1846-1854 (2008)). *Nicotiana benthamiana* plants are then grown and co-agroinfiltrated with the low-endotoxicity GV3101 or LBA4404 strain containing the HBcAg 3' module (pICH11599-HBcAg) along with its 5' TMV module (pICH20999 for ER targeting) and an integrase construct (pICH14011) as described previously (Chen, 2013, Virus-like Particle Vaccines for Norovirus Gastroenteritis. In M. Giese (Ed.), *Molecular Vaccines* (Vol. 1, pp. 153-181). Vienna: Springer; Chen et al., *Advanced Technology in Biology and Medicine*, 1(1), 103-112 (2013); Lai & Chen, 2012; Lai et al., *Plant Cell Reports*, 31(3), 573-584 (2010); Leuzinger et al., *Journal of Visualized Experiments* (77) (2013). Plant leaves can be then harvested 7-10 days after *agrobacterium* infiltration and VLPs can be purified by methods as previously described (reviewed in (Chen & Lai, *Immunotherapeutics*, 9(1), 26-49 (2013)).

Producing Antibody-Based Therapeutics Against Infectious Diseases and Cancer:

Monoclonal antibodies (mAbs) have been very successful as blockbuster drugs against cancer and are being developed for various infectious diseases. MAbs and its derivatives (e.g. scFv-Fc, bifunctional mAbs, and immune complex) have been successfully produced in plants against West Nile virus, Dengue virus, Ebola virus, and various cancers (Dent et al., *Journal of General Virology*, 97(12), 3280-3290 (2016); He et al., *PLoS ONE*, 9(3), e93541 (2014); Lai et al., *Proceedings of the National Academy of Sciences of the United States of America*, 107(6), 2419-2424 (2010); Phoolcharoen, Bhoo, et al., *Plant Biotechnology Journal*, 9(7), 807-816 (2011); Phoolcharoen, Dye, et al., Phoolcharoen, Dye, et al., *Proceedings of the National Academy of Sciences of the United States of America*, 108(51), 20695-20700 (2011)). However, LPS introduced by *Agrobacterium* has to be eliminated by expensive downstream purification process. In this case, antibody light (LC) and heavy chain (HC) genes can be cloned into the 5' modules of plant expression vectors pICH21595 and pICH11599 of the MagnICON system as described previously (Dent et al., *Journal of General Virology*, 97(12), 3280-3290 (2016); He et al., *PLoS ONE*, 9(3), e93541 (2014); Lai et al., *Proceedings of the National Academy of Sciences of the United States of America*, 107(6), 2419-2424 (2010); Phoolcharoen, Bhoo, et al., *Plant Biotechnology Journal*, 9(7), 807-816 (2011); Phoolcharoen, Dye, et al., Phoolcharoen, Dye, et al., *Proceedings of the National Academy of Sciences of the United States of America*, 108(51), 20695-20700 (2011)). Plant expression vectors are then individually transformed into the low-endotoxic *Agrobacterium tumefaciens* GV3101 or LBA4404 strains by electroporation as previously described (Dent et al., *Journal of General Virology*, 97(12), 3280-3290 (2016); He et al., *PLoS ONE*, 9(3), e93541 (2014); Lai et al., *Proceedings of the National Academy of Sciences of the United States of America*, 107(6), 2419-2424 (2010); Phoolcharoen, Bhoo, et al., *Plant Biotechnology Journal*, 9(7), 807-816 (2011); Phoolcharoen, Dye, et al., Phoolcharoen, Dye, et al., *Proceedings of the National Academy of Sciences of the United States of America*, 108(51), 20695-20700 (2011)). *N. benthamiana* plants are grown in a greenhouse with 16/8 hour light/dark cycle at 25° C. for 5 weeks. Plant leaves were co-agroinfiltrated with the low endotoxic GV3101 or LBA4404 strains containing the LC and HC 5' modules along with their respective 3' modules and an integrase construct as described previously (Giritch et al., *Proceedings of the National Academy of Sciences of the United States of America*, 103(40), 14701-14706 (2006)). Agroinfiltrated *N. benthamiana* leaves are then harvested on days 4-10 days post infiltration (dpi) and total leaf protein is extracted by homogenization with extraction buffer (PBS, 1 mM EDTA, 10 mg/ml sodium ascorbate, 10 µg/ml leupeptin, 0.3 mg/ml phenylmethylsufonylflouride) using a FastPrep machine (Bio101) following the manufacture's instruction. The crude plant extract is clarified by centrifugation at 14,000×g for 10 minutes at 4° C. MAbs from the clarified extract can be further purified by a three-step purification protocol comprised of ammonium sulfate precipitation, protein A affinity and DEAE-anion exchange chromatographies as described previously (Lai et al., *Proceedings of the National Academy of Sciences of the United States of America*, 107(6), 2419-2424 (2010)).

Producing Vaccines in Edible Plants for Oral Delivery:

VLPs and other subunit vaccines can also be produced in edible plants such as lettuce for oral immunization, which is easier to admit and more efficacious for pathogens that infect mucosal surface (Chen & Davis, *The potential of plants as a system for the development and production of human biologics* (Vol. 5) (2016); Kwon & Daniell, *Plant Biotechnology Journal*, 13(8), 1017-1022 (2015); Lai, He, Engle, Diamond, & Chen, *Plant Biotechnology Journal*, 10(1), 95-104 (2012)). The presence of LPS from *agrobacterium* prevent the application of such strategy. In such case, the low endotoxic strain of GV3101 or LBA4404 can be used to deliver genes of subunit vaccines or other biologics into edible plant leaves as described previously (Lai et al., *Plant Cell Reports*, 31(3), 573-584 (2012); Liu Clarke et al., *Plant Biotechnology Journal*, doi:10.1111/pbi.12743). The edible plant material with low or none LPS content can be feed to target subjects with minimal processing or purification (Liu Clarke et al., *Plant Biotechnology Journal*, doi:10.1111/pbi.12743).

Producing Vaccines, Antibody-Based Therapeutics and Therapeutic Enzymes in Plant Cell Culture:

In addition to whole plants, *Agrobacterium* can also be used to delivery transgene into plant culture cells such as tobacco BY-2 Cells or carrot cells (Ramloch-Lorenz, Knudsen, & Sturm, *Plant J*, 4(3), 545-554 (1993)) for production of vaccines, mAbs and therapeutic enzymes. For example, carrot-cell produced Human Glucocerebrosidase (commercial name ELELYSO) has been approved by FDA to treat type I Gaucher disease (Aviezer et al., *PLoS ONE*, 4(3), e4792 (2009)). A "drinkable" version of this drug is being developed with carrot cells that contains the glucocerebrosidase (Shaaltiel et al., *Plant Biotechnology Journal*, 13(8), 1033-1040 (2015)). In this case, *Agrobacterium* variants having reduced endotoxicity are useful for reducing the overall LPS content of the drug.

The foregoing and other advantages of the invention have been described in terms of one or more exemplary or preferred embodiments, and it should be appreciated that many equivalents, alternatives, variations, and modifications, aside from those expressly stated, are possible and within the scope of the invention.

We claim:

1. A genetically modified strain of *Agrobacterium*, wherein the genetically modified strain comprises a functional deletion of one or more polypeptides required for synthesis of Very Long Chain Fatty Acid (VLCFA) and is deficient in Lipopolysaccharide (LPS) toxicity relative to its parent strain;
   wherein the functional deletion is achieved by removal of at least a portion of the gene encoding AcpXL-dependent lipid A acyltransferase (lpxXL) and at least a portion of the gene encoding Acyl carrier protein (acpXL), and
   wherein the genetically modified strain comprises an exogenous nucleic acid encoding Lipid A 4'-phosphatase (LpxF), and
   wherein the genetically modified bacterium retains the ability to mediate T-DNA transfer into plant cells, and to mediate T-DNA insertion into a plant cell genome.

2. The modified strain of claim 1, wherein the modified strain produces tetra-acylated lipid A lacking VLCFA.

3. The modified strain of claim 1, wherein the modified strain produces penta-acylated lipid A with VLCFA replaced by a 16:0 acyl chain or 18:1 acyl chain.

4. The modified strain of claim 1, wherein the modified strain produces a mixture of tetra- and penta-acylated lipid A.

5. The modified strain of claim 1, wherein the parent strain is *A. tumefaciens* GV3101 or *A. tumefaciens* LBA4404.

6. The modified strain of claim 1, wherein the parent strain is *A. tumefaciens* strain C58.

7. A method or reducing Lipopolysaccharide (LPS) toxicity in an *Agrobacterium* bacterium, the method comprising: deleting or disrupting at least a portion of a gene encoding AcpXL-dependent lipid A acyltransferase (IpxXL) and at least a portion of a gene encoding Acyl carrier protein (acpXL) in the bacterium, wherein the deletion or disruption comprises a functional deletion;
   introducing an exogenous nucleic acid encoding Lipid A 4'-phosphatase (LpxF) into the bacterium; whereby a genetically modified *Agrobacterium* is obtained;
   wherein the genetically modified *Agrobacterium* exhibits lower LPS toxicity than an unmodified *Agrobacterium*, and
   wherein the genetically modified *Agrobacterium* retains the ability to mediate T-DNA transfer into plant cells, and to mediate T-DNA insertion into a plant cell genome.

8. The method of claim 7, wherein the *Agrobacterium* bacterium is *Agrobacterium tumefaciens* strain GV3101 or LBA4404.

9. The method of claim 7, wherein the *Agrobacterium* bacterium is *Agrobacterium tumefaciens* strain C58.

10. A method for generating a LPS variant molecule having reduced endotoxicity and improved immunogenicity, the method comprising the steps of:
    (a) providing the modified *Agrobacterium* strain of claim 1;
    (b) allowing the modified *Agrobacterium* strain to grow under conditions to produce a LPS variant molecule having reduced endotoxicity and improved immunogenicity compared to an LPS molecule relative to its parent strain.

11. A lipopolysaccharide (LPS) isolated from a genetically modified *Agrobacterium* of claim 1, wherein the LPS exhibits reduced toxicity relative to LPS produced by a wild-type *Agrobacterium* or an *Agrobacterium* that is not so genetically modified.

12. An adjuvant comprising an immunostimulatory quantity of the reduced toxicity LPS of claim 11 and a pharmaceutically acceptable carrier.

* * * * *

UNITED STATES PATENT AND TRADEMARK OFFICE
CERTIFICATE OF CORRECTION

PATENT NO. : 11,130,956 B2  
APPLICATION NO. : 16/617971  
DATED : September 28, 2021  
INVENTOR(S) : Qiang Chen et al.

Page 1 of 1

It is certified that error appears in the above-identified patent and that said Letters Patent is hereby corrected as shown below:

In the Specification

Column 3, Line 29, "a IVIES buffer" should be --a MES buffer--.

Column 3, Line 35, "or IVIES" should be --or MES--.

In the Claims

Column 17, Claim 7, Line 32, "method or reducing" should be --method of reducing--.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*